United States Patent
Rieger (10) Patent No.: US 7,688,443 B2
(45) Date of Patent: Mar. 30, 2010

(54) MULTIPULSE AGILE LASER SOURCE FOR REAL TIME SPARK SPECTROCHEMICAL HAZARD ANALYSIS

(75) Inventor: Harry Rieger, San Diego, CA (US)

(73) Assignee: JMAR LLC, San Diego, CA (US)

( * ) Notice: Subject to any disclaimer, the term of this patent is extended or adjusted under 35 U.S.C. 154(b) by 262 days.

(21) Appl. No.: 11/548,678

(22) Filed: Oct. 11, 2006

(65) Prior Publication Data

US 2007/0195322 A1    Aug. 23, 2007

Related U.S. Application Data

(60) Provisional application No. 60/725,455, filed on Oct. 11, 2005.

(51) Int. Cl.
*G01J 3/30* (2006.01)
(52) U.S. Cl. .................................................. 356/318
(58) Field of Classification Search ................ 356/317, 356/318
See application file for complete search history.

(56) References Cited

U.S. PATENT DOCUMENTS

| | | | | |
|---|---|---|---|---|
| 3,482,184 A | * | 12/1969 | Sharp et al. | ............... 372/23 |
| 3,564,454 A | * | 2/1971 | Dishington et al. | ........... 372/33 |
| 3,818,373 A | * | 6/1974 | Chun et al. | ............... 372/12 |
| 3,879,686 A | * | 4/1975 | Milam et al. | ............... 372/25 |
| 4,326,175 A | * | 4/1982 | Dehney et al. | ............ 372/106 |
| 4,851,664 A | | 7/1989 | Rieger | |
| 5,081,361 A | | 1/1992 | Rieger | |
| 5,095,487 A | * | 3/1992 | Meyerhofer et al. | ........... 372/23 |
| 5,162,940 A | | 11/1992 | Brandelik | |
| 5,361,275 A | * | 11/1994 | Opower | .................. 372/108 |
| 5,434,875 A | | 7/1995 | Rieger et al. | |
| 5,491,707 A | | 2/1996 | Rieger et al. | |
| 5,606,588 A | * | 2/1997 | Umstadter et al. | ........... 378/119 |
| 5,720,894 A | * | 2/1998 | Neev et al. | ................ 216/65 |
| 5,742,634 A | | 4/1998 | Rieger et al. | |
| 5,790,574 A | | 8/1998 | Rieger et al. | |
| 6,008,897 A | * | 12/1999 | Sabsabi et al. | ............. 356/318 |
| 6,016,324 A | | 1/2000 | Rieger et al. | |

(Continued)

OTHER PUBLICATIONS

PCT/US2007/081127, Written Opinion and Search Report of the International Searching Authority dated May 5, 2008.

(Continued)

*Primary Examiner*—Kara E Geisel
(74) *Attorney, Agent, or Firm*—Procopio Cory Hargreaves & Savitch LLP; Noel C. Gillespie (57) ABSTRACT

A sample analysis system comprises a laser unit and a spectrometer unit. The laser unit emits a first laser pulse and a second laser pulse towards the sample with a pulse separation time of between about 1 microsecond to 20 microseconds. The laser unit includes an oscillator unit which is configured to generate the first laser pulse and the second laser pulse. A pre-amplifier unit is configured to receive the first laser pulse and the second laser pulse and increase the energy levels of each pulse prior to the pulses being emitted from the laser unit. The spectrometer unit captures emissions generated by the sample after the sample is stuck by the first and second laser pulses and identifies the elemental constituents of the sample using the emissions.

44 Claims, 8 Drawing Sheets

U.S. PATENT DOCUMENTS

| | | | | |
|---|---|---|---|---|
| 6,078,606 | A * | 6/2000 | Naiman et al. | 372/97 |
| 6,156,030 | A * | 12/2000 | Neev | 606/10 |
| 6,199,794 | B1 * | 3/2001 | Naiman et al. | 244/3.16 |
| 6,292,504 | B1 * | 9/2001 | Halmos | 372/97 |
| 6,356,575 | B1 * | 3/2002 | Fukumoto | 372/97 |
| 6,482,199 | B1 * | 11/2002 | Neev | 606/10 |
| 6,532,068 | B2 * | 3/2003 | Detalle et al. | 356/318 |
| 6,661,511 | B2 * | 12/2003 | Detalle et al. | 356/318 |
| 6,697,394 | B2 * | 2/2004 | Tuennermann et al. | 372/26 |
| 6,760,356 | B2 * | 7/2004 | Erbert et al. | 372/93 |
| 6,873,419 | B2 * | 3/2005 | Detalle et al. | 356/479 |
| 7,106,439 | B2 * | 9/2006 | Lacour et al. | 356/318 |
| 7,116,688 | B2 * | 10/2006 | Sauter et al. | 372/25 |
| 2002/0093653 | A1 * | 7/2002 | Detalle et al. | 356/318 |
| 2003/0016353 | A1 * | 1/2003 | Detalle et al. | 356/318 |
| 2004/0057475 | A1 * | 3/2004 | Frankel et al. | 372/25 |
| 2006/0018349 | A1 * | 1/2006 | Kopf et al. | 372/30 |
| 2007/0047601 | A1 * | 3/2007 | Yu | 372/25 |

OTHER PUBLICATIONS

Brachmann et al., Laser Development for Future Photocathode Research at SLAC. Stanford Linear Accelerator Center, SLAC-PUB-11373, Jul. 31, 2005, pp. 1-4.

Crane et al., Description and Performance of the Preamplifier for the National Ignition Facility (NIF) Laser System. 2nd Annual International Conference on Solid-State Lasers for Application to Inertial Confinement Fusion, Lawrence Livermore National Laboratory, Dec. 19, 1996, pp. 1-8.

* cited by examiner

MULTIPULSE AGILE LASER SOURCE FOR REAL TIME SPARK SPECTROCHEMICAL HAZARD ANALYSIS

CROSS-REFERENCE TO RELATED APPLICATIONS

This application claims priority under 35 U.S.C. 20 to U.S. Provisional Patent Application No. 60/725,455, filed Oct. 11, 2005, entitled "Multipulse Agile Laser Source for Real Time Spark Spectrochemical Hazard Analysis in the Field." The contents of which are incorporated herein in its entirety as if set forth full.

BACKGROUND

1. Field of the Invention

The embodiments disclosed in this application generally relate to methods, apparatuses, and systems for generating multiple laser pulses in short succession for use in laser induced breakdown spectroscopy systems to characterize materials via spectrochemical analysis.

2. Background of the Invention

Laser induced breakdown spectroscopy (LIBS) is an analytical method that uses a laser to ablate and ionize a sample, forming a plasma from which light emitted from the plasma can be analyzed to identify the elemental constituents of the sample. LIBS techniques are well suited for field analysis since only the laser beam must reach the sample. This is especially advantageous for remote sample monitoring of hazardous materials or materials located in difficult to reach locations. Lasers systems suitable for use in LIBS systems typically have good spatial beam quality and a high enough pulse energy to adequately ionize the material being analyzed, which is particularly important when the sample being analyzed has a relatively large standoff distance from the LIBS system.

LIBS systems using conventional laser systems have resulted in issues with high detection limits (typically >1 ppm), reproducibility of results, and interference due to matrix effects (that is low signal to noise ratios that interfere with the analysis). Many of these issues can be traced back to the variations in the laser spark and resultant plasma process due to shortcomings with the laser systems used. In short, existing laser systems used in LIBS systems and methods for spectrochemical analysis fail to provide the optimal detection limit, reproducibility, and signal to noise ratio parameters required for achieving optimal real time spectrochemical hazard analysis in the field.

SUMMARY

Methods, systems, and apparatuses for generating multiple laser pulses in short succession for use in LIBS systems are disclosed.

In one aspect, a system for analyzing a sample is disclosed. The system is comprised of a laser unit and a spectrometer unit. The laser unit is configured to emit a first laser pulse and a second laser pulse towards the sample with a pulse separation time of between about 1 microsecond to 20 microseconds. The laser unit includes an oscillator unit, a pre-amplifier unit and an amplifier unit. The oscillator unit is configured to generate the first laser pulse and the second laser pulse. The pre-amplifier unit is configured to receive the first laser pulse and the second laser pulse and increase the energy levels of each pulse to a first energy state. The amplifier unit is configured to receive the first laser pulse and the second laser pulse from the pre-amplifier unit and further increase the energy levels of each pulse to a second energy level prior to the pulses being emitted from the laser unit. The spectrometer unit is configured to capture emissions generated by the sample after the sample is struck by the first and second laser pulses then characterize the sample using the emissions.

In a different aspect, another system for analyzing a sample is disclosed. The system is comprised of a laser unit and a spectrometer unit. The laser unit is configured to emit a first laser pulse and a second laser pulse towards the sample with a pulse separation time of between about 1 microsecond to 20 microseconds. The laser unit includes an oscillator unit and an amplifier unit. The oscillator unit is configured to generate the first laser pulse and the second laser pulse. The amplifier unit is configured to receive the first laser pulse and the second laser pulse from the pre-amplifier unit and increase the energy levels of each pulse to a first energy level prior to the pulses being emitted from the laser unit. The spectrometer unit is configured to capture emissions generated by the sample after the sample is struck by the first and second laser pulses then characterize the sample using the emissions.

In another aspect, a laser unit for emitting multiple laser pulses is disclosed. The laser unit is comprised of an oscillator unit, a pre-amplifier unit, and an amplifier unit. The oscillator unit is configured to generate a first laser pulse and a second laser pulse with a pulse separation time of between about 1 microseconds and 20 microseconds.

The oscillator unit includes a laser gain medium, a laser pumping unit, a first Pockels cell, and a second Pockels cell. The laser gain medium is configured to be pumped to an excited energy state and emit a photon beam. The laser pumping unit is positioned proximate to the laser gain medium and pump the laser gain medium. The first Pockels cell and the second Pockels cell are configured to receive the photon beam emitted by the laser gain medium and to toggle between an activated state and deactivated state. The second Pockels cell is further configured to work in conjunction with the first Pockels cell to convert the excited energy state into the first laser pulse and the second laser pulse by each respectively toggling between the activated state and the deactivated state.

The pre-amplifier unit is configured to receive the first laser pulse and the second laser pulse from the oscillator unit and increase the energy levels of each pulse to a first energy state. Whereas, the amplifier unit is configured to receive the first laser pulse and the second laser pulse form the pre-amplifier unit and further increase the energy levels of each pulse to a second energy state prior to the first laser pulse and the second laser pulse being emitted from the laser unit.

In still another aspect, a laser unit for emitting multiple laser pulses is disclosed. The laser unit is comprised of an oscillator unit and an amplifier unit. The oscillator unit is configured to generate a first laser pulse and a second laser pulse with a pulse separation time of between about 1 microseconds and about 20 microseconds.

The oscillator unit includes a laser gain medium, a laser pumping unit, a first Pockels cell, and a second Pockels cell. The laser gain medium is configured to be pumped to an excited energy state and emit a photon beam. The laser pumping unit is positioned proximate to the laser gain medium and pump the laser gain medium. The first Pockels cell and the second Pockels cell are configured to receive the photon beam emitted by the laser gain medium and to toggle between an activated state and deactivated state. The second Pockels cell is further configured to work in conjunction with the first Pockels cell to convert the excited energy state into the first laser pulse and the second laser pulse by each respectively toggling between the activated state and the deactivated state.

The amplifier unit is configured to receive the first laser pulse and the second laser pulse from the oscillator unit and increase the energy levels of each pulse to a first energy state prior to the first laser pulse and the second laser pulse being emitted from the laser unit.

In yet another aspect, a method for analyzing a sample is disclosed. A sample is ablated with a first laser pulse of laser light. The sample is ionized with a second pulse of laser light. Atomic emissions discharged from the sample after the sample is ionized with the second pulse of laser light is captured. The atomic emissions are diffracted into individual emission lines. The individuals emission lines are detected. The sample is characterized based on the individual emission lines detected.

In one more aspect, a method for generating multiple laser pulses is disclosed. A gain medium is pumped to an excited energy state using an external energy source. A first Pockels cell is activated. A first laser pulse is discharged including a first portion of energy from the gain medium. A second Pockels cell is activated after a time delay that determines a duration time of the first laser pulse. The first Pockels cell is deactivated after a second time delay that is between about 1 microseconds and about 20 microseconds. A second laser pulse is discharged including a remaining portion of energy from the gain medium.

These and other features, aspects, and embodiments of the invention are described below in the section entitled "Detailed Description."

BRIEF DESCRIPTION OF THE DRAWINGS

For a more complete understanding of the principles disclosure herein, and the advantages thereof, reference is now made to the following descriptions taken in conjunction with the accompanying drawings, in which.

DETAILED DESCRIPTION

The embodiments described below are directed to methods, systems, and apparatuses for generating multiple laser pulses in short succession for use in LIBS systems. It will be obvious, however, that the embodiments described can be practiced without some or all of these specific details. In other instances, well known process operations have not been described in detail in order not to unnecessarily obscure the present embodiments.

As used herein, laser pumping is a process by which a laser gain medium (e.g., laser rod, laser head, etc.) is energized via a transfer of energy from an external energy source. The energy is absorbed in the medium, producing excited states in the gain medium atoms. When the number of particles in an excited state exceeds the number of particles in a ground state or a less-excited state, a condition known as population inversion is achieved. In this condition, the mechanism of stimulated emission (i.e., laser beam emission) can take place and the medium can act as a laser or an optical amplifier.

A Pockels cell is a voltage controlled (through a constant or varying electric field) optical medium that utilizes the principles behind the Pockels effect to alter the polarization state of light that travels through the medium. A typical Pockels cell is a transparent crystalline medium that becomes birefringent whenever a constant or varying electric field is applied against the medium. This property of a Pockels cell causes light that passes through the cell to emerge having a different linear polarization state (i.e., optical rotation). The changed polarization state or optical rotation of the light traveling through the Pockels cell depends on the wavelength retardation characteristics of the cell. For example, a Pockels cell that effectuates a quarter wavelength phase shift ($\lambda/4$) shifts the optical rotation of linearly polarized light traveling through the cell by about 90 degrees (along an axis of rotation that is perpendicular to the propagation direction of the light), whereas a Pockels cell that effectuates a half wavelength phase shift ($\lambda/2$) shifts the optical rotation of the light by about 180 degrees and so on.

A cube polarizer is a beam splitting polarization device that is configured to split an incident beam into two beams of differing polarization states (e.g., "s" or "p" polarization component). The typical cube polarizer operates by reflecting either the "s" or "p" polarization component of a light beam and directing the reflected component at an incident angle (typically about 90 degrees) relative to the incident direction of the light beam.

An optical cavity is a region between two or more high reflectivity mirrors that resonates light waves (i.e., optical beams) that enter the cavity by bouncing the wave back and forth between the mirrors within the cavity. As more light wave energy enters the cavity, the energy within the cavity can combine with and reinforce the standing wave, increasing its intensity. This is done through pumping wherein an incident light wave that enters the optical cavity can be resonant by bouncing back and forth within the cavity. Within the context of a laser optical cavity, a laser gain medium (e.g., laser rod, laser head, etc.) is used as the means by which light wave energy is transferred to the standing wave via laser pumping of the laser gain medium. When the gain medium reaches a state where the number of particles in one excited state exceeds the number of particles in some lower-energy state, population inversion is achieved. In this condition, a light wave passing through the medium produces more stimulated emission than stimulated absorption, so the light wave (i.e., optical beam) is amplified. During the amplification process each photon beam (i.e., light) passes through the gain medium more than once before being emitted from the output aperture (i.e., output coupler) or lost to diffraction or absorption.

Figure 1:
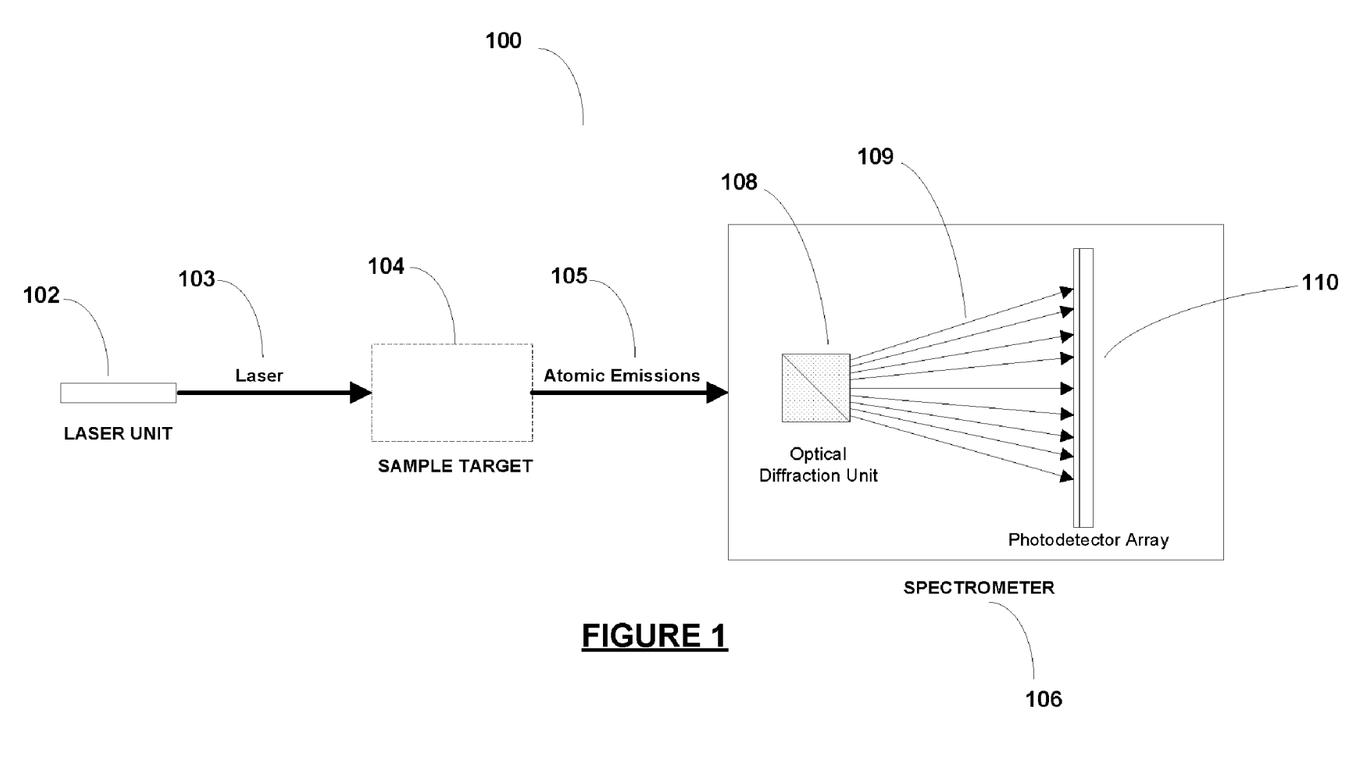
FIG. 1 is an illustration of how a laser induced breakdown spectroscopy (LIBS) system may be configured, in accordance with one embodiment.

FIG. 1 is an illustration of how a laser induced breakdown spectroscopy (LIBS) system may be configured, in accordance with one embodiment. In this depiction, the LIBS system 100 includes a laser unit 102, a sample target 104, and a spectrometer unit 106. The laser unit 102 is configured to emit a laser beam 103 that strikes a sample target 104 and ionizes (i.e., excitation) the target's 104 constituent atoms. When those constituent atoms return to a non-excited state, they discharge atomic emissions 105 that are characteristic for each of the atomic constituents of the sample target 104. In one embodiment, the laser unit 102 has a master oscillator power amplifier (MOPA) configuration. It should be appreciated, however, that the laser unit 102 may use any type of laser power amplification configuration as long as the resulting laser unit 102 is capable of discharging multiple laser pulses 103 with a pulse separation time of between 1 microsecond ($\mu s$) and 200 $\mu s$, with a pulse 103 duration time of between 1 nanosecond (ns) and 20 ns, and at a pulse 103 energy level of between about 50 millijoules (mJ) and 300 mJ.

In one embodiment, the laser unit 102 is configured to emit two laser pulses 103 within a time span of between about 1 $\mu s$ and about 10 $\mu s$. The first pulse 103 is used to ablate the sample target 104, while the second pulse 103 ionizes the sample target 104. This multi-pulse operation of the laser unit 102 serves to improve the sensitivity of the LIBS system 100 and the overall reproducibility of results as the interference effects due to the composition of the sample target 104 is negated by the first laser pulse 103.

The discharged atomic emissions 105 is captured by a spectrometer 106 that is configured to analyze the atomic emissions 105 and characterize the atomic makeup (i.e., chemically identify) of the sample target 104. It should be appreciated that the LIBS system 100 configuration depicted in FIG. 1 is presented for illustrative purposes only and is in no way intended to limit the available LIBS system 100 configurations in any way. There are a multitude of approaches to setting up a LIBS system 100 depending on the needs of the particular application and limited only by the ability of the resulting LIBS system 100 to analyze a target sample 104 with the required analytical reproducibility and sensitivity.

As depicted in FIG. 1, the spectrometer 106 includes an optical diffraction unit 108 and a photodetector array 110. The optical diffraction unit 108 is configured to capture the atomic emissions (i.e., light) 105 discharged from the sample target 104 and spatially separate (i.e., diffract) the atom emission lines 109 and direct them towards the individual photodetectors arranged on the photodetector array 110. In one embodiment, the diffraction unit 108 is a simple prism. In another embodiment, the diffraction unit 108 is a polychromator. In still another embodiment, the diffraction unit 108 is a diffraction grating. It should be understood that the diffraction unit 108 can be any type of light transforming apparatus as long as the apparatus can function to adequately disperse the atomic emissions 105 emitted by an ionized sample target 104 such that the atomic emissions 105 can be detected and characterized using a photodetector array 110.

The elemental constituents of the target sample 104 are identified depending on which photodetectors on the array 110 are illuminated by the atomic emission lines 109. For example, when a sample target 104 consisting of carbon, oxygen, and chlorine atoms is ionized by a laser beam 103 discharged from the laser unit 102 the sample emits atomic emissions 105 that are characteristic for the elemental makeup of the sample. The atomic emissions 105 are spatially separated by the optical diffraction unit 108 into separate atomic emission lines 109 that are directed towards individual photodetectors arranged on the array 110. The elemental constituents of the sample 104 are identified depending on which photodetectors on the array 110 registers an atomic emission line 109 strike. In one embodiment, the photodetector array 110 is comprised of a plurality of charged coupled devices (CCD). In another embodiment, the photodetector array 110 is comprised of a plurality of photomultipliers. It should be appreciated, however, that the photodetector array 110 can be comprised of essentially any type of photodetector as long as the photodetector has the requisite sensitivity to light required for the particular application.

Figure 2A:
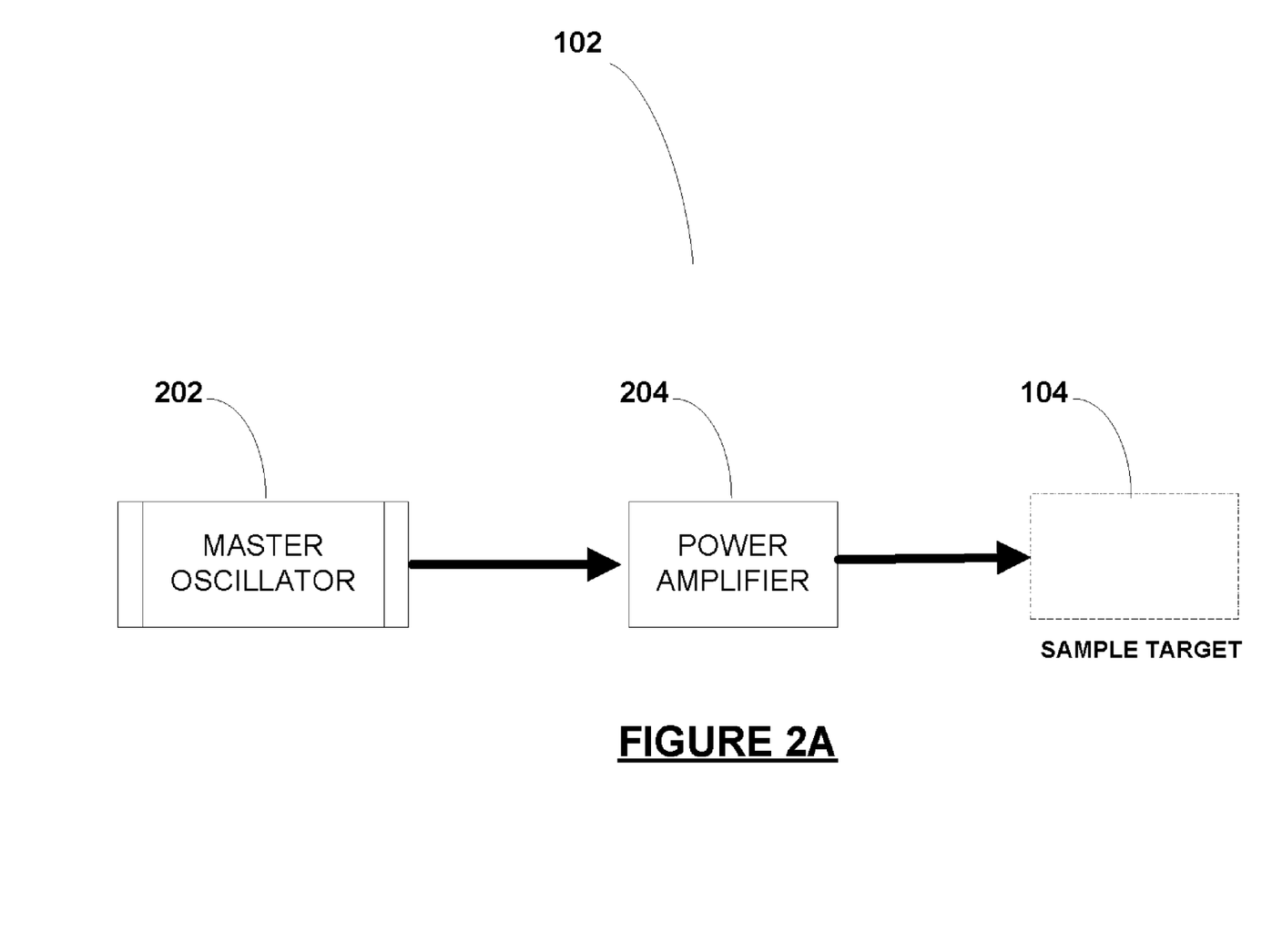
FIG. 2A is a schematic depiction of a MOPA laser unit with an amplification module, in accordance with one embodiment.

FIG. 2A is a schematic depiction of a MOPA laser unit with an amplification module, in accordance with one embodiment. As depicted herein, the laser unit 102 includes a master oscillator unit 202 and a power amplifier module 204. The power amplifier module 204 is configured to receive laser beam pulses emitted by the master oscillator unit 202. In one embodiment, the master oscillator unit 202 is configured to emit laser beam pulses with a power output of about 1 millijoule (mJ). In another embodiment, the master oscillator unit 202 is configured to emit laser beam pulses with a power output of between about 1 mJ and about 10 mJ. It should be understood that the master oscillator unit 202 can be configured to emit laser beam pulses with any power output as long as the operational limits of the master oscillator unit 202 is not exceeded and the laser beam pulses can be modified to have a diffraction limited beam quality (i.e., $M^2$ value) of less than about 1.5.

The power amplifier module 204 is configured to amplify the power of the laser beam pulse received from the master oscillator 202 to a pre-determined amplification factor and discharge the amplified laser beam pulse towards the sample target 104. In one embodiment, the power amplifier module 204 is configured to amplify the power of the laser beam pulse by an amplification factor of between about 10 and about 500. In another embodiment, the power amplifier module 204 is configured to amplify the power of the laser beam pulse by an amplification factor of between about 25 and about 250. It should be understood, however, that the power amplifier module 204 can be configured to amplify the laser beam pulse to any amplification factor as long as the operational limits of the power amplifier module 204 is not exceeded by the amplification operation and the resulting amplified pulse has a diffraction limited beam quality (i.e., $M^2$ value) of less than about 1.5.

Figure 2B:
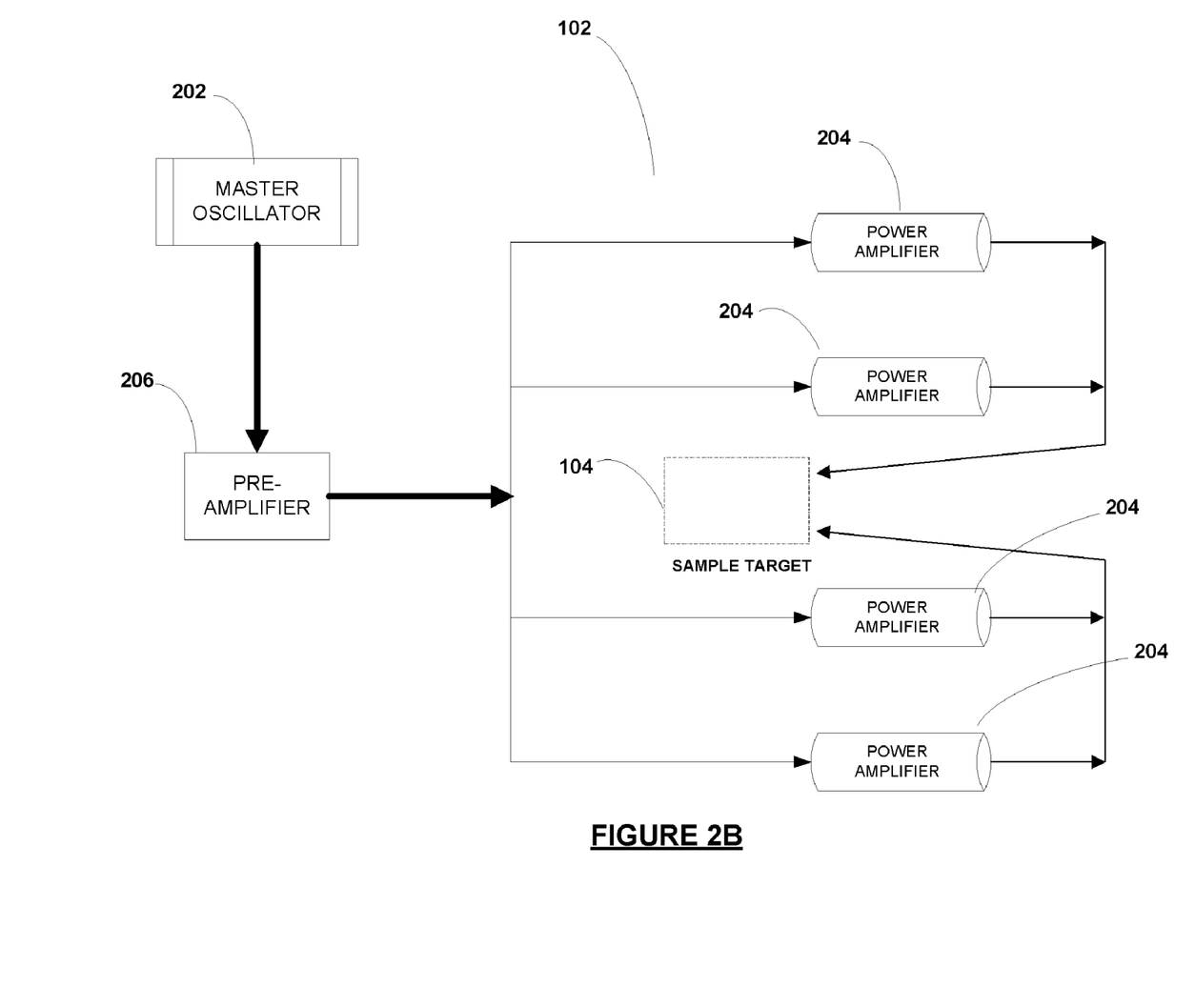
FIG. 2B is a schematic illustration of a MOPA laser unit with a pre-amplifier module and four parallel power amplifier modules, in accordance with one embodiment.

FIG. 2B is a schematic illustration of a MOPA laser unit with a pre-amplifier module and four parallel power amplifier modules, in accordance with one embodiment. In this depiction, the laser unit 102 includes a master oscillator 202, a pre-amplifier module 206 and four power amplifier modules 204 arranged in parallel. It should be appreciated that the laser unit 102 can be configured to include up to eight parallel amplifier modules 204 depending on the requirements of the particular application. The master oscillator unit 202 is configured to emit a laser beam pulse towards the pre-amplifier module 206. The pre-amplifier module 206 is configured to amplify the power of the laser beam pulse by a predetermined amplification factor, split the laser beam pulse into four equal laser output beams, and align each beam with one of the four parallel aligned power amplifier modules 204. In one embodiment, the pre-amplifier module 206 is configured to utilize a four pass amplification scheme to amplify the laser beam power by an amplification factor of about 100. In another embodiment, the amplification factor is between about 2 and 200. It should be appreciated, however, that the pre-amplifier module 206 can be configured to amplify the laser beam pulse by any amplification factor as long as the operational limits of the pre-amplifier module 206 is not exceeded by the amplification operation and the resulting amplified pulse can be modified to have a diffraction limited beam quality (i.e., $M^2$ value) of less than about 1.5.

Each power amplifier module 204 is configured to amplify the power of the laser beam pulse received from the pre-amplifier module 206 to a pre-determined amplification factor and discharge the amplified laser beam towards the sample target 104. In one embodiment, each of the four parallel aligned power amplifier modules 204 utilizes a four pass amplification scheme to amplify the laser beam power by an amplification factor of about 10. In another embodiment, each of the four parallel aligned power amplifier modules 204 are configured to amplify the laser beam power by an amplification factor of between about 2 to about 20. It should be understood, however, that each power amplifier module 204 can be configured to amplify the laser beam pulse by any amplification factor as long as the operational limits of the power amplifier module 204 is not exceeded by the amplification operation and the resulting amplified pulse has a diffraction limited beam quality (i.e., $M^2$ value) of less than about 1.5.

Figure 3A:
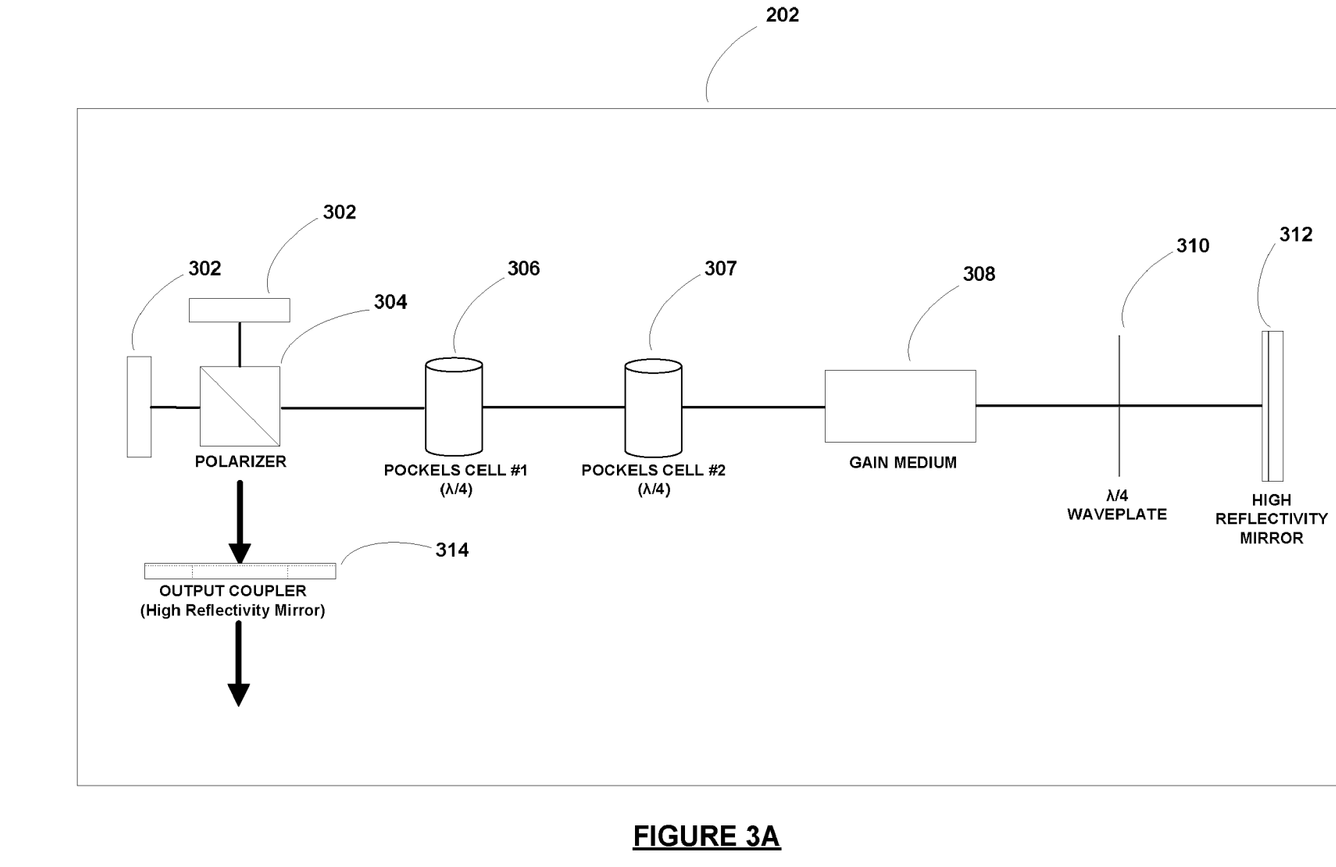
FIG. 3A is a schematic layout of a master oscillator used to generate multiple laser pulses using Pockels cells, in accordance with one embodiment.

FIG. 3A is a schematic layout of a master oscillator used to generate multiple laser pulses using Pockels cells, in accordance with one embodiment. As depicted herein, the master oscillator unit 202 includes an output coupler 314, a polarizer 304, a pair of beam dumps 302, a first Pockels cell 306, a second Pockels cell 307, a gain medium 308, a quarter wavelength ($\lambda/4$) waveplate 310, and a high reflectivity mirror 312. In one embodiment, the master oscillator unit 202 is configured to generate multiple laser beam pulses containing about 1 mJ of energy. In another embodiment, the master oscillator unit 202 is configured to generate multiple laser beam pulses containing between about 1 mJ and about 10 mJ of energy. It should be appreciated, however, that the master oscillator unit 202 may be configured to generate multiple laser beam pulses containing any quantity of energy as long as the operating parameters of the master oscillator 202 is not exceeded and the resulting pulses can be modified to have a diffraction limited beam quality (i.e., $M^2$ value) of less than about 1.5.

In one embodiment, the gain medium 308 is comprised of a crystalline neodymium doped yttrium aluminum garnet (Nd:YAG) material. In another embodiment, the gain medium 308 is comprised of a ceramic-based material. It should be appreciated that the gain medium 308 can be comprised of essentially any type of material as long as the medium 308 can be utilized by the master oscillator unit 202 to generate multiple laser beam pulses that have a diffraction limited beam quality (i.e., $M^2$ value) of less than about 1.5 containing between about 1 mJ and about 10 mJ of energy.

Within the master oscillator unit 202, the region between the output coupler 314 and the high reflectivity mirror 312 is termed the laser optical cavity. The gain medium 308 is configured to be pumped by an external energy source, positioned proximate to the medium 308, to achieve a population inversion state. In one embodiment, the external energy source is an optical energy source such as a diode array or a flash lamp. In another embodiment, the external energy source is an electrical based energy source wherein an electric current is used to pump the gain medium 308. In still another embodiment, the external energy source is an electromagnetic (EM) radiation source that uses microwaves or their equivalents to pump the gain medium 308.

Once the gain medium 308 reaches a population inversion state, a beam of photons is emitted from the gain medium 308 within the laser optical cavity of the master oscillator unit 202. The beam can travel in either of two opposing directions depending on how the gain medium 308 is configured. In one embodiment, the gain medium 308 is configured to emit a beam of photons towards the beam splitting polarizer 304 through the second Pockels cell 307 and the first Pockels cell 306. When the beam reaches the polarizer 304, the beam is directed by the polarizer 304 to either the beam dumps 302 or the output coupler 314. The beam splitting polarizer 304 is configured to direct the beam to either the beam dump 302 or the output coupler 314 based on the polarization state of the input beam of photons. For example, in one embodiment, the beam splitting polarizer 304 is configured to direct a beam of photons having a "p" polarization state towards the output coupler 314 and a beam having a "s" polarization (that is about 90 degrees shifted from the "p" polarization state) state towards the beam dumps 302. In another embodiment, the beam splitting polarizer 304 is configured to direct a beam of photons having the "p" polarization state towards the beam dumps 302 and a beam having the "s" polarization state towards the output coupler.

The output coupler 314 is configured to be partially transmissive to allow a portion of the photon beam to be discharged from the master oscillator unit 202 and reflect the remaining portion of the beam back towards the high reflectivity mirror 312. Once reflected, the photon beam resonates (travels back and forth) within the laser optical cavity and continues to draw additional photons (i.e., amplify) from the gain medium through every pass until the beam is either emitted through the output coupler 314 or is directed by the polarizer to be dissipated by the beam dumps 302.

Figure 4:
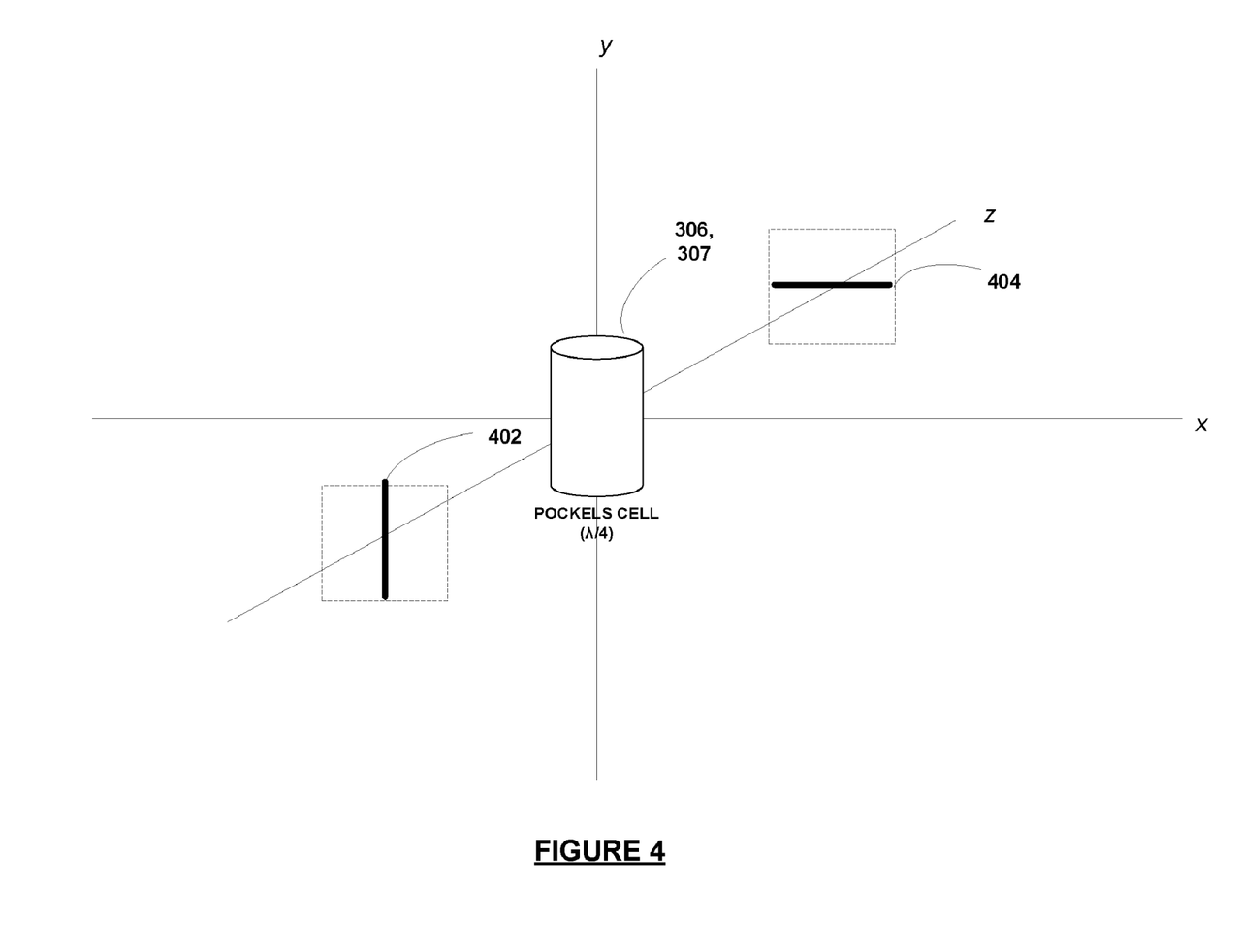
FIG. 4 is an illustration of a photon beam having a "p" polarization state being shifted into a beam having a "s" polarization state after traveling through an activated Pockels cell, in accordance with one embodiment.

As depicted in FIG. 3A, when either of the Pockels cells (i.e. the first Pockels cell 306 and the second Pockels cell 307) are activated, they are configured to shift an incident photon beam by a quarter wavelength ($\lambda/4$) as the beam travels through the cell. This has the net effect of rotating the polarization state of the incident beam by about 90 degrees. For example, as depicted in FIG. 4, a photon beam having a "p" polarization state 402 is shifted into a beam having a "s" polarization state 404 (about 90 degrees rotated from the "p" polarization state) after traveling through an activated Pockels cell (306, 307). When the Pockels cell (306, 307) is set to a deactivated state, the incident beam travels through the deactivated Pockels cell (306, 307) unchanged. It should be understood that the Pockels cells (i.e., the first Pockels cell 306 and the second Pockels cell 307) in the master oscillator unit 202 of FIG. 3A may be configured to effectuate any wavelength shift ($\lambda/n$) as long as the optical rotation (i.e. polarization state) of the output photon beam from each Pockels cell differs from that of the incident photon beam entering each Pockels cell. In one embodiment, the Pockels cells are configured to toggle between an activated state and deactivated state in less than about 1 µs. In another embodiment, the Pockels cells are configured to toggle between an activated state and deactivated state in between about 1 µs and about 200 µs.

Continuing with FIG. 3A, in one embodiment, the gain medium 308 is configured to emit a photon beam towards the high reflectivity mirror 312 through the quarter wavelength waveplate 310. The quarter wavelength waveplate 310 is configured to shift the polarization state of the photon beam by a quarter wavelength ($\lambda/4$), or about 90 degrees, as the beam travels through the waveplate 310. Typically, the waveplate 310 is configured to unidirectionally shift the polarization state of the photon beam. This means that the polarization state of the beam is shifted only when it travels through the waveplate 310 towards the high reflectivity mirror 312 and not when the beam travels through the waveplate 310 towards the gain medium 308. The high reflectivity mirror 312 is configured to reflect the beam from the waveplate 310 back towards the beam splitting polarizer 304 and then to either the beam dumps 302 or the output coupler 314 depending on the polarization state of the beam, the setting of the beam splitting polarizer 304 and whether either of the Pockels cells are in an activated state.

For example, in one embodiment, the beam splitting polarizer 304 is set to direct an "s" polarized photon beam toward the beam dumps 302 and a "p" polarized (about 90 degrees shifted from the "s" polarized laser beam) photon beam toward the output coupler 314. Therefore, when a "s" polarized photon beam is emitted from the gain medium 308, the beam is shifted into a "p" polarized photon beam as the beam passes through the waveplate 310 and then reflected off the high reflectivity mirror 312 back in the direction of the beam splitting polarizer 304. If both of the Pockels cells (i.e., the first Pockels cell 306 and the second Pockels cell 307) are in a deactivated state, the "p" polarized laser beam passes through them unchanged before reaching the beam splitting polarizer 304, which then directs the beam towards the output coupler 314. If either of the Pockels cells are in an activated state, the reflected "p" polarized laser beam is shifted back into a "s" polarized laser beam before reaching the beam splitting polarizer 304, which directs the beam towards the beam dumps 302.

In one embodiment, the Pockels cells (i.e., the first Pockels cell 306 and the second Pockels cell 308) are configured to be toggled between an activated state and a deactivated state such that the master oscillator unit 202 can emit multiple laser beam pulses within a time span of between about 1 µs and about 200 µs having a pulse duration time of between about 1 nanoseconds (ns) and about 20 ns. During the operation of the master oscillator unit 202 to generate multiple laser beam pulses, both of the Pockels cells (i.e., the first Pockels cell 306 and the second Pockels cell 307) are initially set to a deactivated state. The gain medium 308 is configured to generate a "p" polarized photon beam towards the quarter wavelength waveplate 310. The polarizer 304 is configured to direct a "s" polarized beam towards the beam dumps 302 and a "p" polarized beam towards the output coupler 314. As the gain medium 308 is pumped by an external energy source (e.g., diode array, flash lamp, etc.) to reach the population inversion state, the medium 308 emits a beam of photons that travels towards the quarter wavelength waveplate 310. The beam of photons emitted from the gain medium 308 is a "p" polarized beam when the beam reaches the quarter wavelength waveplate 310.

As discussed above, when the "p" polarized beam travels through the quarter wavelength waveplate 310, the polarization state of the beam is shifted by about 90 degrees into a "s" polarized beam. In this state, when the beam reflects back from the high reflectivity mirror 312 through the Pockels cells and the beam splitting polarizer 304, the beam is directed towards the beam dumps 302 thus preventing the feedback of the photon beam into the laser optical cavity. This prevents the optical amplification of the photon beam and allows the gain medium 308 to be pumped to a highly excited state. When the medium 308 becomes saturated by energy, the first Pockels cell 306 is activated and the beam is shifted back into a "p" polarized beam that is directed by the polarizer 304 towards the output coupler 314 allowing the photon beam to resonate within the laser optical cavity. The beam is then amplified by the gain medium 308 until the beam surpasses the lasing threshold of the laser optical cavity and is emitted through the output coupler 314 as a first laser beam pulse. The first laser beam pulse continues to be emitted by the output coupler 314 until the second Pockels cell 307 is activated to shift the photon beam back into a "s" polarized beam, which results in the beam being directed by the polarizer 304 to the beam dumps 302; stopping the beam amplification and terminating the laser action. The time delay between the activation of the first Pockels 306 cell and the activation of the second Pockels cell 307 equals the duration time of the first laser beam pulse.

When the first Pockels cell 306 is toggled into a deactivated state the beam is again shifted back into a "p" polarized beam, which results in the beam being directed to output coupler 314; starting the beam amplification process again and producing a second laser beam pulse. The second beam pulse is terminated when the second Pockels cell 307 is toggled into a deactivated state. The time delay between the deactivation of the first Pockels cell 306 and the deactivation of the second Pockels cell 307 equals the duration time of the second laser beam pulse. In this manner, both the first laser beam pulse and the second laser beam pulses are collinear as they are both emitted as "p" polarized beams.

Figure 3B:
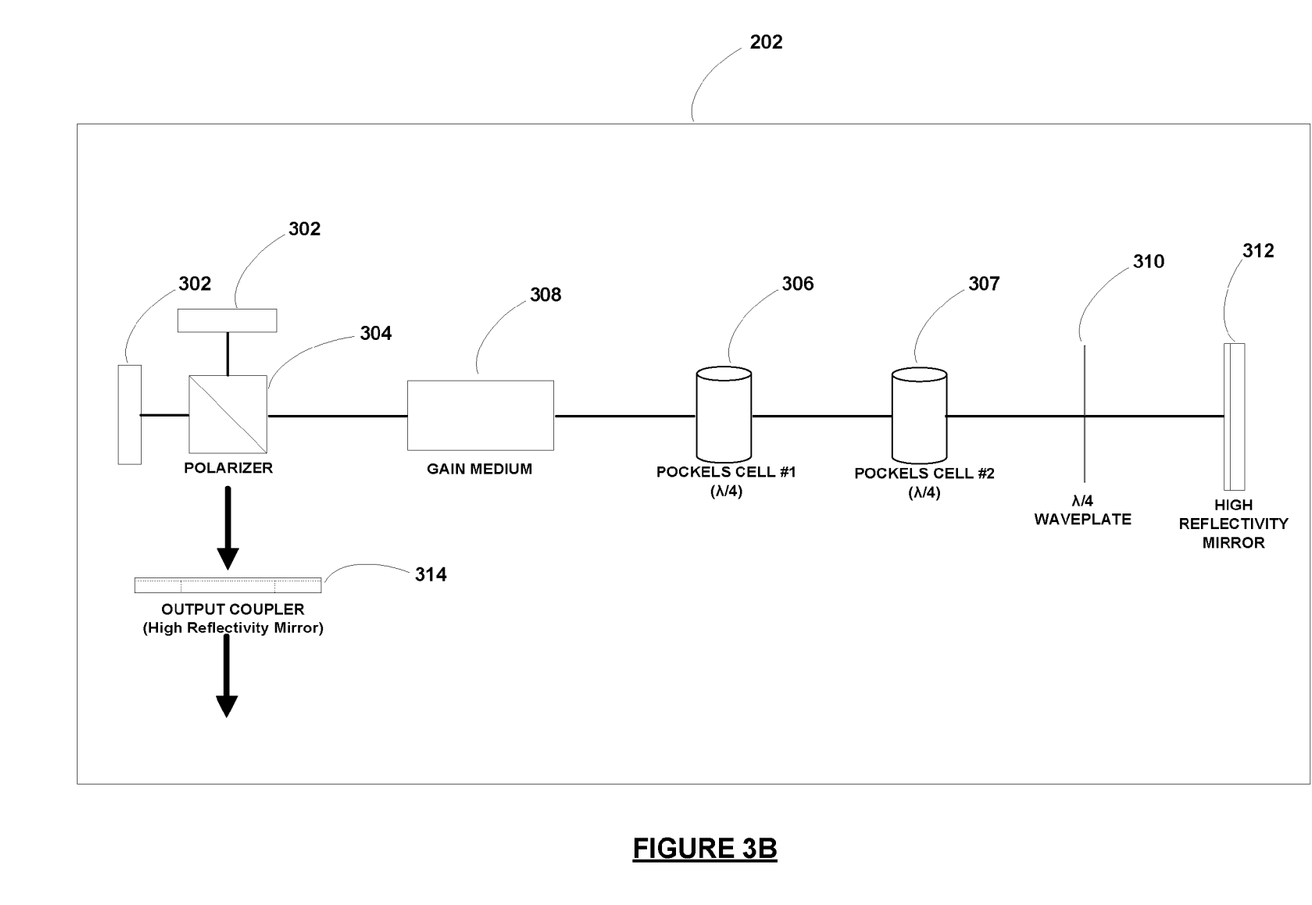
FIG. 3B, is a schematic layout of a master oscillator where the Pockels cells are positioned between the gain medium and the quarter wavelength waveplate, in accordance with one embodiment.
Figure 3C:
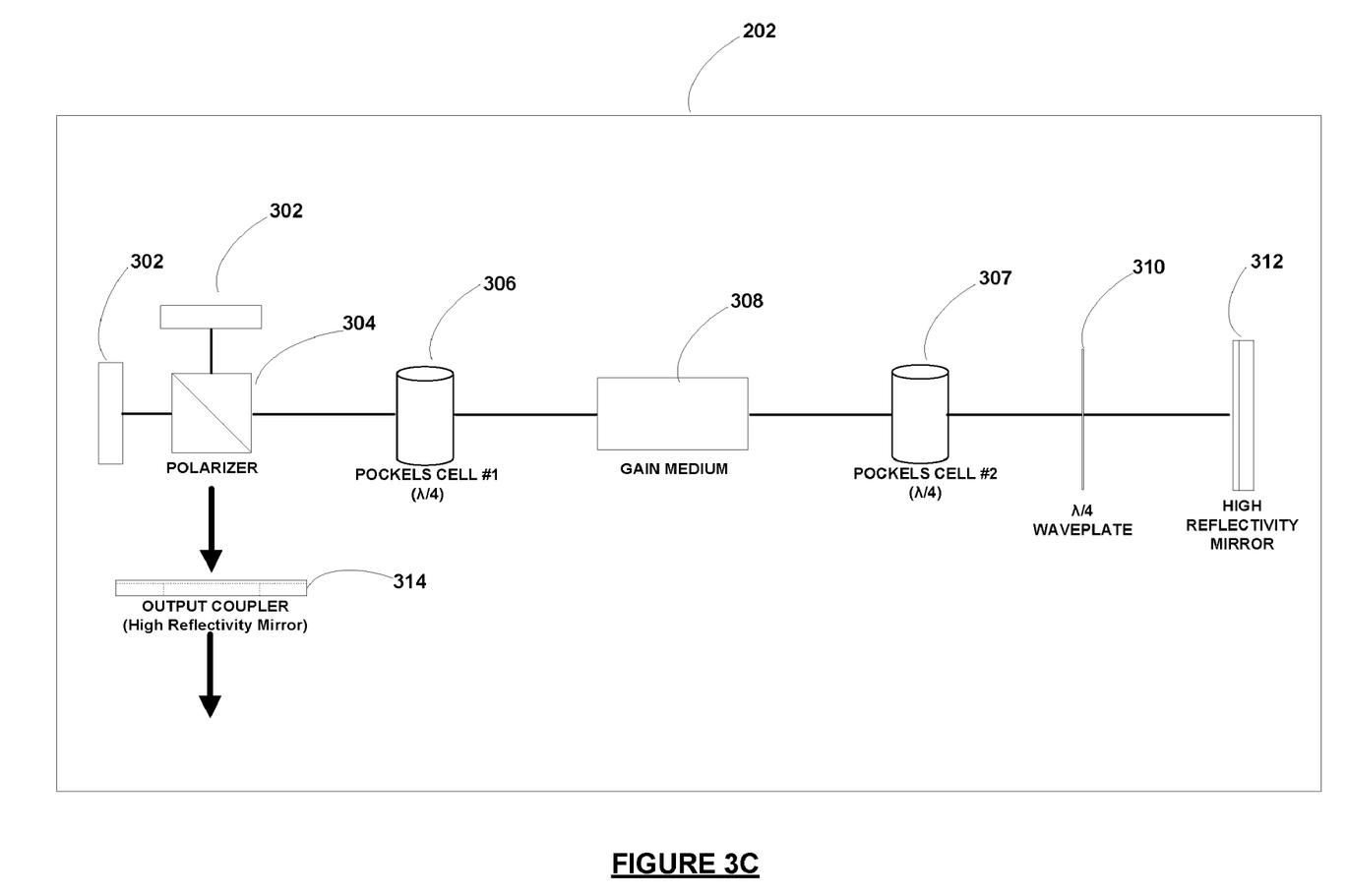
FIG. 3C, is a schematic layout of a master oscillator a Pockels cell is positioned on both sides of the gain medium, in accordance with one embodiment.

The positions of the Pockels cells in relation to the gain medium 308 may be varied without negating the ability of the Pockels cells to be utilized by the master oscillator 202 to emit multiple laser pulses within a time span of between about 1 µs and about 200 µs having a pulse duration time of between about 1 nanoseconds (ns) and about 20 ns. For example, in one embodiment as depicted in FIG. 3B, the Pockels cells (the first Pockels cell 306 and the second Pockels cell 307) are positioned between the gain medium 308 and the quarter wavelength waveplate 310. In another embodiment, as depicted in FIG. 3C, a Pockels cell is positioned on both sides of the gain medium 308. In both configurations, the Pockels cells may still be toggled between an activated state and deactivated state in the same or similar manner as that described above to emit multiple laser beam pulses from the master oscillator unit 202.

Figure 5:
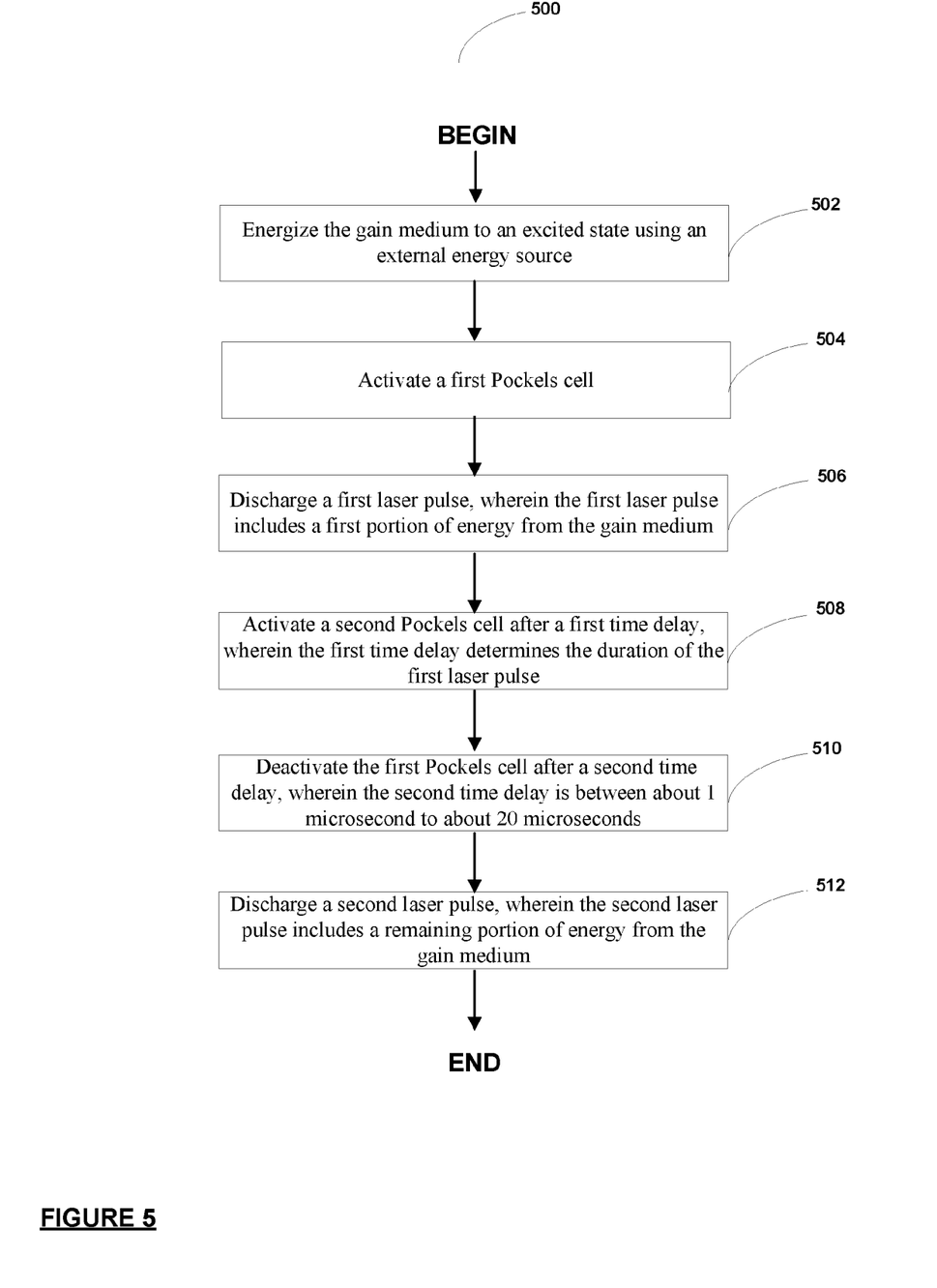
FIG. 5 shows a flowchart of a method of toggling the activation states of two Pockels cell units to produce multiple laser pulses, in accordance with one embodiment.

FIG. 5 shows a flowchart of a method 500 of toggling the activation states of two Pockels cell units to produce multiple laser pulses, in accordance with one embodiment. Diagrams of the system utilized in this method are shown in FIGS. 3A and 4. Method 500 begins with operation 502 where the gain medium is energized using an external energy source. In one embodiment, the gain medium is comprised of a crystalline neodymium doped yttrium aluminum garnet (Nd:YAG) material. In another embodiment, the gain medium is comprised of a ceramic-based material. It should be appreciated that the gain medium can be comprised of essentially any type of material as long as the medium can be utilized by the master oscillator unit to generate multiple laser beam pulses that have a diffraction limited beam quality (i.e., $M^2$ value) of less than about 1.5 and contain between about 1 mJ and about 10 mJ of energy.

In one embodiment, the external energy source is an optical energy source such as a diode array or a flash lamp. In another embodiment, the external energy source is an electrical based energy source wherein an electric current is used to pump the gain medium. In still another embodiment, the external energy source is an electromagnetic (EM) radiation source that uses microwaves or their equivalents to pump the gain medium.

The method then proceeds to operation 504 where a first Pockels cell is activated. In one embodiment, the first Pockels cell is configured to toggle between an activated state and deactivated state in less than about 1 µs. In another embodiment, the first Pockels cell is configured to toggle between an activated state and deactivated state in between about 1 µs and about 200 µs.

The method continues on to operation 506 where a first laser beam pulse is discharged by the master oscillator unit. The first laser beam pulse contains a portion of the energy that was pumped into the gain medium during operation 502. In one embodiment, the first laser beam pulse has a power output of about 1 millijoule (mJ). In another embodiment, the first laser beam pulse has a power output of between about 1 mJ and about 10 mJ.

The method moves on to operation 508 where the second Pockels cell is activated after a first time delay. The first time delay determines the duration time of the first laser pulse. In one embodiment, the first time delay is between about 1 nanoseconds (ns) and about 20 ns. In another embodiment, the first time delay is between about 3 ns and 6 ns. It should be understood that the first time delay may be set to any value as long as the first laser pulse does not drain the entire energy content of the gain medium.

The method next progresses to operation 510 where the first Pockels cell is deactivated after a second time delay that is between about 1 μs and about 20 μs. Upon deactivation of the second Pockels cell, the method progresses to operation 512 where a second laser beam pulse is discharged containing the remaining portion of energy held by the gain medium after the discharge of the first laser beam pulse. The duration of the second time delay equals the pulse separation time between the first laser beam pulse and the second laser beam pulse.

Although a few embodiments of the present invention have been described in detail herein, it should be understood, by those of ordinary skill, that the present invention may be embodied in many other specific forms without departing from the spirit or scope of the invention. Therefore, the present examples and embodiments are to be considered as illustrative and not restrictive, and the invention is not to be limited to the details provided therein, but may be modified and practiced within the scope of the appended claims.

What is claimed is:

1. A system for analyzing a sample, comprising:
a laser unit configured to emit a first laser pulse and a second laser pulse towards the sample with a pulse separation time of between about 1 microseconds and about 20 microseconds, wherein the laser unit includes,
an oscillator unit configured to generate the first laser pulse and the second laser pulse, a pre-amplifier unit configured to receive the first laser pulse and the second laser pulse from the oscillator unit and increase energy levels of each pulse to a first energy state, the pre-amplifier unit increasing the energy profile of each pulse by a factor of between about 2 to about 100, and
an amplifier unit configured to receive the first laser pulse and the second laser pulse from the pre-amplifier unit and further increase the energy levels of each pulse to a second energy state prior to the first laser pulse and the second laser pulse being emitted from the laser unit; and
a spectrometer unit configured to capture emissions generated by the sample after the sample is struck by the first laser pulse and the second laser pulse, wherein the spectrometer unit is further configured to identify the elemental constituents of the sample using the emissions.

2. The system for analyzing a sample, as recited in claim 1, wherein the first laser pulse and the second laser pulse has a beam quality that is diffraction limited.

3. The system for analyzing a sample, as recited in claim 1, wherein the first laser pulse and the second laser pulse are collinear.

4. The system for analyzing a sample, as recited in claim 1, wherein the oscillator unit uses a crystalline laser rod to generate the first laser pulse and the second laser pulse.

5. The system for analyzing a sample, as recited in claim 4, wherein the crystalline laser rod is comprised of crystalline neodymium doped yttrium aluminum garnet (Nd:YAG) material.

6. The system for analyzing a sample, as recited in claim 1, wherein the first laser pulse and the second laser pulse has a pulse duration of between about 3 nanoseconds and about 6 nanoseconds.

7. The system for analyzing a sample, as recited in claim 1, wherein the spectrometer is further connected to a collection optic unit by way of a fiber optic cable, the collection optic unit configured to capture emissions generated by the sample and transmit the emissions to the spectrometer via the fiber optic cable.

8. The system for analyzing a sample, as recited in claim 1, wherein the energy level of the first laser pulse and the second laser pulse is between about 100 millijoules (mJ) to about 250 mJ.

9. A system for analyzing a sample, comprising:
a laser unit configured to emit a first laser pulse and a second laser pulse towards the sample with a pulse separation time of between about 1 microseconds and about 20 microseconds, wherein the laser unit includes,
an oscillator unit configured to generate the first laser pulse and the second laser pulse, the oscillator unit including,
a laser gain medium configured to be pumped to an excited energy state and emit a photon beam after reaching the excited energy state,
a laser pumping unit configured to pump the laser gain medium, a first Pockels cell configured to receive the photon beam emitted by the laser gain medium and to toggle between activated and deactivated states, and
a second Pockels cell configured to receive the photon beam emitted by the laser gain medium and to toggle between activated and deactivated states,
wherein the combined states of the first and second Pockels cells control discharge of a first laser pulse and a second laser pulse towards the sample and the pulse separation time between the pulses, the first Pockels cell being configured to toggle from a deactivated state to an activated state to control discharge of a first laser pulse including a first portion of energy from the laser gain medium, the second Pockels cell being configured to toggle from a deactivated state to an activated state after a first time delay, wherein the first time delay determines a duration time of the first laser pulse, and the first Pockels cell being configured to toggle between an activated state and a deactivated state after a second time delay which determines the pulse separation time between the first and second laser pulses, the second laser pulse including a second portion of energy from the laser gain medium;
a pre-amplifier unit configured to receive the first laser pulse and the second laser pulse from the oscillator unit and increase energy levels of each pulse to a first energy state prior to the first laser pulse and the second laser pulse being emitted from the laser unit; and
a spectrometer unit configured to capture emissions generated by the sample after the sample is struck by the first laser pulse and the second laser pulse, wherein the spectrometer unit is further configured to identify the elemental constituents of the sample using the emissions.

10. The system for analyzing a sample, as recited in claim 9, wherein the first laser pulse and the second laser pulse has a beam quality that is diffraction limited.

11. The system for analyzing a sample, as recited in claim 9, wherein the first laser pulse and the second laser pulse are collinear.

12. The system for analyzing a sample, as recited in claim 9, wherein the oscillator unit uses a crystalline laser rod to generate the first laser pulse and the second laser pulse.

13. The system for analyzing a sample, as recited in claim 12, wherein the crystalline laser rod is comprised of crystalline neodymium doped yttrium aluminum garnet (Nd:YAG) material.

14. The system for analyzing a sample, as recited in claim 9, wherein the first laser pulse and the second laser pulse has a pulse duration of between about 3 nanoseconds and about 6 nanoseconds.

15. The system for analyzing a sample, as recited in claim 9, wherein the pre-amplifier unit increases the energy levels of each pulse is increased by a factor of between about 2 to about 100.

16. The system for analyzing a sample, as recited in claim 9, wherein the spectrometer is further connected to a collection optic unit by way of a fiber optic cable, the collection optic unit configured to capture emissions generated by the sample and transmit the emissions to the spectrometer via the fiber optic cable.

17. The system for analyzing a sample, as recited in claim 9, wherein the energy level of the first laser pulse and the second laser pulse is between about 100 millijoules (mJ) to about 250 mJ.

18. A laser unit for emitting multiple laser pulses, comprising:
    an oscillator unit configured to generate a first laser pulse and a second laser pulse with a pulse separation time of between about 1 microseconds and about 20 microseconds, the oscillator unit including,
    a laser gain medium configured to be pumped to an excited energy state and emit a photon beam after reaching the excited energy state,
    a laser pumping unit positioned proximate to the laser gain medium, the laser pumping unit configured to pump the laser gain medium,
    a first Pockels cell configured to receive the photon beam emitted by the laser gain medium, wherein the first Pockels cell is further configured to toggle between an activated state and a deactivated state, and
    a second Pockels cell configured to receive the photon beam emitted by the laser gain medium, wherein the second Pockels cell is further configured to toggle between an activated state and a deactivated state,
    wherein the first Pockels cell is configured to toggle from a deactivated state to an activated state to control discharge of the first laser pulse including a first portion of the energy from the laser gain medium towards the sample, and the second Pockels cell is further configured to toggle from a deactivated state to an activated state after a first time delay after discharge of the first laser pulse, wherein the first time delay determines a duration time of the first laser pulse,
    the first Pockels cell being further configured to toggle between an activated state and a deactivated state after a second time delay to control discharge of the second laser pulse including a second portion of the energy from the laser gain medium towards the sample, and
    the first laser pulse and the second laser pulse having a time duration of between about 3 nanoseconds and about 6 nanoseconds
    a pre-amplifier unit configured to receive the first laser pulse and the second laser pulse from the oscillator unit and increase energy levels of each pulse to a first energy state; and
    an amplifier unit configured to receive the first laser pulse and the second laser pulse from the pre-amplifier unit and to further increase the energy levels of each pulse to a second energy state prior to the first laser pulse and the second laser pulse being emitted from the laser unit.

19. The laser unit, as recited in claim 18, wherein the first laser pulse and the second laser pulse has a beam quality that is diffraction limited.

20. The laser unit, as recited in claim 18, wherein the first laser pulse and the second laser pulse are collinear.

21. The laser unit, as recited in claim 18, wherein the oscillator unit uses a crystalline laser gain medium to generate the first laser pulse and the second laser pulse.

22. The laser unit, as recited in claim 21, wherein the crystalline laser gain medium is comprised of crystalline neodymium doped yttrium aluminum garnet (Nd:YAG) material.

23. The laser unit, as recited in claim 18, wherein the pre-amplifier unit increases the energy levels of each pulse is increased by a factor of between about 2 to about 100.

24. The laser unit, as recited in claim 18, wherein the energy level of the first laser pulse and the second laser pulse is between about 100 millijoules (mJ) to about 250 mJ.

25. The laser unit, as recited in claim 18, wherein the laser pumping unit is a diode array.

26. The laser unit, as recited in claim 18, wherein the laser pumping unit is a flash lamp unit.

27. A laser unit for emitting multiple laser pulses, comprising:
    an oscillator unit configured to generate a first laser pulse and a second laser pulse with a pulse separation time of between about 1 microseconds and about 20 microseconds, the oscillator unit including,
    a laser gain medium configured to be pumped to an excited energy state and emit a photon beam,
    a laser pumping unit positioned proximate to the laser gain medium, the laser pumping unit configured to pump the laser gain medium,
    a first Pockels cell configured to receive the photon beam emitted by the laser gain medium, wherein the first Pockels cell is further configured to toggle between an activated state and a deactivated state, and
    a second Pockels cell configured to receive the photon beam emitted by the laser gain medium, wherein the second Pockels cell is further configured to toggle between an activated state and a deactivated state,
    the first Pockels cell and the second Pockels cell being further configured to work in conjunction to control discharge of the first laser pulse and the second laser pulse towards the sample and the pulse separation time between the first and second pulses by each respectively toggling between the activated state and the deactivated state,
    wherein the first Pockels cell is configured to toggle from a deactivated state to an activated state to control discharge of the first laser pulse including a first portion of the energy from the laser gain medium towards the sample, the second Pockels cell is configured to toggle from a deactivated state to an activated state after a first time delay after discharge of the first laser pulse, wherein the first time delay determines a duration time of the first laser pulse, and the first Pockels cell is further configured to toggle between an activated state and a deactivated state after a second time delay which determines the pulse separation time between the first laser pulse and the second laser pulse, the second laser pulse including a second portion of the energy from the laser gain medium; and
    an amplifier unit configured to receive the first laser pulse and the second laser pulse from the oscillator unit and to further increase energy levels of each pulse to a first energy state prior to the first laser pulse and the second laser pulse being emitted from the laser unit and wherein the energy levels of the first laser pulse and the second laser pulse are between about 100 millijoules (mJ) to about 250 mJ.

28. The laser unit, as recited in claim 27, wherein the first laser pulse and the second laser pulse has a beam quality that is near diffraction limited.

29. The laser unit, as recited in claim 27, wherein the first laser pulse and the second laser pulse are collinear.

30. The laser unit, as recited in claim 27, wherein the oscillator unit uses a crystalline laser gain medium to generate the first laser pulse and the second laser pulse.

31. The laser unit, as recited in claim 30, wherein the crystalline laser gain medium is comprised of crystalline neodymium doped yttrium aluminum garnet (Nd:YAG) material.

32. The laser unit, as recited in claim 27, wherein the first laser pulse and the second laser pulse has a pulse duration of between about 3 nanoseconds and about 6 nanoseconds.

33. The laser unit, as recited in claim 27, wherein the pre-amplifier unit increases the energy levels of each pulse is increased by a factor of between about 2 to about 100.

34. The laser unit, as recited in claim 27, wherein the laser pumping unit is a diode array.

35. The laser unit, as recited in claim 27, wherein the laser pumping unit is a flash lamp unit.

36. A method for analyzing a sample, comprising:
pumping a laser gain medium to an excited energy state using an external energy source;
activating a first Pockels cell;
discharging a first pulse of laser light towards a sample and ablating the sample with the first pulse of laser light, wherein the first pulse includes a first portion of energy from the laser gain medium;
activating a second Pockels cell after a first time delay, wherein the first time delay determines a duration time of the first laser pulse;
deactivating the first Pockels cell after a second time delay, wherein the second time delay is between about 1 microsecond and about 20 microseconds; and
discharging a second pulse of laser light towards the sample and ionizing the sample with the second pulse of laser light, wherein the second pulse includes a remaining portion of energy from the laser gain medium;
wherein each pulse of laser light has a duration time of between about 3 nanoseconds and about 6 nanoseconds;
capturing atomic emissions discharged from the sample after the sample is ionized with the second pulse of laser light;
diffracting the atomic emissions into individual emission lines;
detecting each of the individual emission lines; and
characterizing the sample based on the individual emission lines detected.

37. The method for analyzing a sample, as recited in claim 36, wherein the atomic emissions is captured using a spectrophotometer unit, the spectrophotometer unit including an optical diffraction unit and a photodetector array.

38. The method for analyzing a sample, as recited in claim 37, wherein a time interval of between about 1 microsecond and about 20 microseconds separates the first pulse of laser light and the second pulse of laser light.

39. A method for generating multiple laser pulses, comprising:
pumping a laser gain medium to an excited energy state using an external energy source;
activating a first Pockels cell;
discharging a first laser pulse, wherein the first laser pulse includes a first portion of energy from the laser gain medium;
activating a second Pockels cell after a first time delay, wherein activation of the second Pockels cell determines a duration time of the first laser pulse;
deactivating the first Pockels cell after a second time delay, wherein the second time delay is between about 1 microsecond and about 20 microseconds; and
discharging a second laser pulse including a remaining portion of energy from the laser gain medium, wherein deactivation of the first Pockels cell controls discharge of the second laser pulse and the second time delay defines an interval time between the discharge of the first laser pulse and the second laser pulse.

40. A method for generating multiple laser pulses, comprising:
pumping a laser gain medium to an excited energy state using an external energy source activating a first Pockels cell;
discharging a first laser pulse, wherein the first laser pulse includes a first portion of energy from the laser gain medium;
activating a second Pockels cell after a first time delay, wherein the first time delay determines a duration time of the first laser pulse;
deactivating the first Pockels cell after a second time delay, wherein the second time delay is between about 1 microsecond and about 20 microseconds; and
discharging a second laser pulse, wherein the second laser pulse includes a remaining portion of energy from the laser gain medium;
wherein the energy level is between about 100 millijoules (mJ) and about 250 mJ.

41. A method for generating multiple laser pulses, comprising:
pumping a laser gain medium to an excited energy state using an external energy source;
activating a first Pockels cell;
discharging a first laser pulse, wherein the first laser pulse includes a first portion of energy from the laser gain medium;
activating a second Pockels cell after a first time delay, wherein the first time delay determines a duration time of the first laser pulse;
deactivating the first Pockels cell after a second time delay, wherein the second time delay is between about 1 microsecond and about 20 microseconds; and
discharging a second laser pulse, wherein the second laser pulse includes a remaining portion of energy from the laser gain medium;
wherein the first laser pulse and the second laser pulse ha each have a duration time of between about 3 nanoseconds and about 6 nanoseconds.

42. The method for generating multiple laser pulses, as recited in claim 41, wherein the external energy source is a diode array.

43. The method for generating multiple laser pulses, as recited in claim 41, wherein the external energy source is a flash lamp unit.

44. The method for generating multiple laser pulses, as recited in claim 41, wherein the laser gain medium is a ceramic rod.

* * * * *